United States Patent [19]
Mannschedel

[11] Patent Number: 5,961,250
[45] Date of Patent: Oct. 5, 1999

[54] SUBSTANCE MIXTURE FOR COFFERDAM MATERIAL, COFFERDAM MATERIAL, AND THE USE AND PREPARATION THEREOF

[75] Inventor: Werner Mannschedel, Langenau, Germany

[73] Assignee: ROEKO GmbH & Co., Dentalerzeugnisse, Langenau, Germany

[21] Appl. No.: 08/601,732

[22] Filed: Feb. 15, 1996

[30] Foreign Application Priority Data

Feb. 17, 1995 [DE] Germany ............................ 195 05 496

[51] Int. Cl.⁶ ...................................... E02D 19/04
[52] U.S. Cl. .............................. 405/11; 524/588; 528/12; 528/23; 528/24
[58] Field of Search ............................. 524/588; 405/11; 528/12, 23, 24

[56] References Cited

U.S. PATENT DOCUMENTS

| | | | |
|---|---|---|---|
| 3,785,313 | 1/1974 | Rosenberg | 114/5 T |
| 3,862,081 | 1/1975 | Itoh et al. | 528/32 |
| 4,410,677 | 10/1983 | Lampe | 528/17 |
| 4,487,906 | 12/1984 | Kniege et al. | 528/15 |
| 4,504,065 | 3/1985 | Devine | 277/12 |
| 4,568,707 | 2/1986 | Voigt et al. | 524/773 |
| 4,938,211 | 7/1990 | Takahashi et al. | 128/204.26 |
| 4,965,295 | 10/1990 | Schwabe et al. | 528/31 |
| 5,327,202 | 7/1994 | Nami et al. | 355/282 |
| 5,352,724 | 10/1994 | Fujiki et al. | 524/493 |
| 5,580,921 | 12/1996 | Stepp et al. | 528/15 |

FOREIGN PATENT DOCUMENTS

| | | |
|---|---|---|
| 1471799 | 3/1967 | France . |
| 3423823 | 1/1986 | Germany . |

*Primary Examiner*—Randy Gulakowski
*Attorney, Agent, or Firm*—Burgess, Ryan & Wayne

[57] ABSTRACT

The invention relates to a substance mixture for a material for a cofferdam, to the material, and to the use and preparation thereof.

17 Claims, No Drawings

SUBSTANCE MIXTURE FOR COFFERDAM MATERIAL, COFFERDAM MATERIAL, AND THE USE AND PREPARATION THEREOF

BACKGROUND OF THE INVENTION

1). Field of the Invention

The invention relates to a substance mixture for a cofferdam material, to the material, and to the use and preparation thereof.

2). Background Art

A cofferdam is an aid customarily used in dentistry, for example for dental operations. Synonyms are rubberdam, stretch rubber, rubber cloth and rubber plate.

During dental treatment the cofferdam is arranged in the patient's mouth in the region of the tooth or group of teeth to be treated and can have an extremely wide variety of functions. For example, it may be used to protect the patient from unintentionally breathing or swallowing, it may provide protection from infection for the patient, attendants and dentist, and it may assist in providing an aseptic field of operation and in draining the area being treated, in holding back and protecting soft tissues and in improving visibility and in providing increased access; reference is made, for example, to Winkler, Kofferdam in Theorie und Praxis, Quintessenz-Verlags GmbH, 1991, for example, page 17, FIG. 7; and also Denis & Ott in Dtsch. Zahnärztl. Z., (1993) 303–308.

Such a cofferdam can additionally be provided with a holding device in order that it can be secured in the region of the tooth in the form of a square, rectangular or round protective element.

The main constituent of a cofferdam is usually natural rubber which is obtained from latex. For preparation, the liquid raw latex is coagulated to form a thin film which is subjected to heat vulcanization. The thin rubber material prepared in this manner is marketed in the form of sheets or rolls.

A great problem in the use of customary cofferdams obtained from natural rubber is allergic reaction. It is to be assumed that allergies are attributable to the complex composition of the latex and to additives that are used in the vulcanization of the latex.

DE-A-3 423 823 and EP-A-0 268 347 disclose the use as dental impression compounds of cross-linkable silicones having a content of silicic acid (as filler) and silicone processing auxiliaries. In accordance with DE-A-3 423 823, it is possible to provide a base paste and a catalyst paste that contains platinum as catalyst. The two pastes are mixed together for use and harden at room temperature (Examples 3 and 5). The teaching given by EP-A-0 268 347 corresponds to that prior art and uses platinum black as catalyst.

It is also already known from U.S. Pat. No. 5,098,299 to seal, repair and fit rubberdam with the aid of a composition that is a material having a content of, for example, polydimethylsiloxane, a filler, such as glass particles, a hydrophilising low molecular weight aliphatic glycol and a cellulose material for homogeneity. The plasticity of that material allows compounds introduced into the mouth to be fitted and shaped in situ (column 12 below to column 13 above), for which purpose light-curing materials are selected (column 10, line 33). The properties required of that known composition are said to be guaranteed, for example, for from 0.2 to 4 hours (Example 1).

SUMMARY OF THE INVENTION

It is now a problem of the invention to provide a substance mixture for a material for a cofferdam and to provide a cofferdam material. Those subjects should be simple to produce and easy to process and as far as possible should not trigger undesirable bodily reactions, especially allergies.

It is a further aim of the invention to provide a process for the preparation of the said substance mixture and material that is simple from the manufacturing standpoint.

In accordance with an embodiment, the problem underlying the invention is solved by a substance mixture for a material for cofferdam, comprised of (a) from 56 to 96% by weight silicone rubber (polymer), (b) from 44 to 4% by weight silicic acid (filler), (c) from 1 to 7% by weight customary silicone rubber processing auxiliary (based on (a) and (b) as 100%) and (d) from 0.1 to 1.1% by weight radical-forming cross-linking agent (based on (a) and (b) as 100%) it being possible for the cross-linking agent to be in admixture with components (a) to (c) or to be separate therefrom.

DESCRIPTION OF THE PREFERRED EMBODIMENTS

In accordance with a special embodiment, the substance mixture may contain from 8 to 28%, and especially approximately 20%, by weight silicic acid. The silicic acid serves especially to establish the elasticity, recovery and tensile strength of the material. Highly active pyrogenic silicic acid is especially preferred.

Special preference is given to a substance mixture for a transparent material. A content of color pigments is possible, but in a transparent material the upper limit is reached when the transparency is impaired. It will be self-evident that transparency facilitates observation of the field of operation.

The substance mixture according to the invention may contain an oil, especially a silicone oil, as a silicone rubber processing auxiliary. As cross-linking agents, it is possible to use peroxides, for example a cross-linking agent customary in the rubber industry.

An example of a formulation of a substance mixture according to the invention provides (a) approximately 80% by weight silicone rubber, (b) approximately 20% by weight silicic acid, (c) approximately 4% by weight silicone rubber processing auxiliary (based on (a) and (b) as 100%) and (d) approximately 0.6% by weight radical-forming cross-linking agent (based on (a) and (b) as 100%).

The problem underlying the invention is solved in accordance with a further embodiment by a cofferdam material that can be obtained by hot vulcanization from a substance mixture according to the invention. If there is used for the cofferdam material a substance mixture according to the invention having features (a) to (c), it is possible to use, apart from radical-forming cross-linking agents, also metals, for example platinum, as cross-linking agents for that hot vulcanization.

The material according to the invention is preferably transparent. It can be provided in the form of flat material, especially in the form of round, rectangular or square sheets, and especially having dimensions of approximately 150 mm×approximately 150 mm, and the thickness of the material according to the invention may be from 0.1 to 0.8 mm.

The procedure for preparing a substance mixture according to the invention and a cofferdam material according to the invention is as follows:

(i) (a) from 56 to 96% by weight silicone rubber (polymer), b) from 44 to 4% by weight silicic acid (filler) and from 1 to 7% by weight customary silicone rubber processing auxiliary (based on (a) and (b) as 100%) are mixed to form a premix and optionally (ii) from 0.1 to 1.1% by weight cross-linking agent (based on (a) and (b) as 100%) is then incorporated into the premix, (iii) the resulting mixture is subjected to hot vulcanization under pressure, (iv) the resulting vulcanisate is subjected to a heat treatment, and (v) the heat-treated vulcanisate is processed to form a material according to the invention.

Step (ii) can be carried out with the aid of a roll mill.

If color pigments are provided, they can be incorporated at stage (ii).

For the hot vulcanization of stage (iii), it is possible to subject the mixture obtained in step (ii) to an extrusion, injection-moulding or compression operation. For hot vulcanization, it is possible to use a temperature in the range of from 150 to 180° C. and/or a pressure in the range of from 50 to 140 tons per 225 cm², especially approximately 100 tons per 225 cm².

EXAMPLE

For the preparation of cofferdam, the following components are selected.

8.0 kg silicone rubber 2.0 kg highly active pyrogenic silicic acid 0.4 kg silicone oil The components are mixed together with the aid of a roll mill to form a premix. 60 g of a peroxide customarily used in the rubber industry as a cross-linking agent and also 10 g of an inorganic green pigment are then added to the premix, those additional components being incorporated with the aid of the roll mill.

The resulting mixture is subjected to hot vulcanization under pressure in moulds, sheets of 150×150×0.5 mm being obtained. Those sheets are exposed to a heat treatment in order to decompose unreacted cross-linking agent.

The cofferdam sheets prepared are transparent.

I claim:

1. A cofferdam obtained by vulcanization of a mixture comprised of:

(a) from 56 to 96% by weight of a silicone rubber polymer, (b) from 44 to 4% by weight of a silicic acid filler, (c) from 1 to 7% by weight of a liquid or solid silicone oil based on (a) and (b) as 100% and (d) from 0.1 to 1.1% by weight of a liquid or solid radical forming cross-linking agent to be in admixture with components (a) to (c) or to be separate therefrom.

2. A cofferdam according to claim 1 obtained by vulcanization of a mixture comprised of from 8 to 28% by weight of a silicic acid.

3. A cofferdam according to claim 1 obtained by vulcanization of a mixture comprised of about 20% by weight of a silicic acid.

4. A cofferdam according to claim 1 obtained by vulcanization of a mixture comprised of an oil as a silicone rubber processing auxiliary.

5. A cofferdam according to claim 1 obtained by vulcanization of a mixture comprised of a peroxide as a cross-linking agent.

6. A cofferdam according to claim 1 obtained by vulcanization of a mixture which contains a color pigment.

7. A cofferdam obtained by vulcanization of a mixture of claim 1 and wherein platinum is used as the cross-linking agent.

8. A cofferdam according to claim 1 which is transparent.

9. A cofferdam according to claim 1 characterized in that it is provided in the form of a flat material.

10. A cofferdam according to claim 1 that is in the form of round, rectangular or square sheets, with dimensions of approximately 150 mm×approximately 150 mm.

11. A cofferdam according to claim 1 which has a thickness of from 0.1 to 0.8 mm.

12. A cofferdam obtained by a process which comprises the steps of:

(i) forming a premix of:
      (a) from 56 to 96% by weight of a silicone rubber polymer,
      (b) from 44 to 4% by weight of a silicic acid filler and
      (c) from 1 to 7% by weight of a silicone oil based on (a) and (b) as 100%;

(ii) optionally incorporating into the premix from 0.1 to 1.1% by weight of a cross-linking agent based on (a) and (b) as 100%;

(iii) subjecting the resulting mixture to hot vulcanization under pressure;

(iv) subjecting the resulting vulcanisate to a heat treatment, and (v) processing the heat-treated vulcanisate to form a cofferdam.

13. The material according to claim 12 wherein step (ii) is carried out with the aid of a roll mill.

14. A material according to claim 12 wherein color pigments are incorporated in step (ii).

15. A material according to claim 12 wherein the mixture obtained in step (ii) is subjected to an extrusion, injection-moulding or compression operation for the purpose of hot vulcanization.

16. A material according to claim 15 wherein the hot vulcanization of step (iii) is carried out at a temperature in the range of from 150 to 180° C. and/or at a pressure in the range of from 50 to 140 tons/225 cm².

17. A material according to claim 16 wherein the vulcanization pressure is 100 tons/225 cm².

\* \* \* \* \*